United States Patent [19]

Morita et al.

[11] Patent Number: 5,202,342

[45] Date of Patent: Apr. 13, 1993

[54] N-ALKYL THIAZOLIDINE DERIVATIVES

[75] Inventors: Takakazu Morita, Toyonaka; Shiro Mita, Ashiya; Yoichi Kawashima, Kyoto, all of Japan

[73] Assignee: Santen Pharmaceutical Co., Ltd., Osaka, Japan

[21] Appl. No.: 725,012

[22] Filed: Jul. 3, 1991

[30] Foreign Application Priority Data

Jul. 18, 1990 [JP] Japan .................. 2-191070

[51] Int. Cl.$^5$ ............... C07D 277/14; A61K 31/425
[52] U.S. Cl. ................... 514/369; 548/186; 548/187
[58] Field of Search ............. 548/186, 187; 514/369

[56] References Cited

U.S. PATENT DOCUMENTS 4,148,800  4/1979  Schubert .................. 548/182

OTHER PUBLICATIONS

Johnston J. Org. Chem. 29, 2442(1964).
Soai, Heterocycles, 22 (12) 2827 (1984).
Yoshimitsu Nagao et al, "Syntheses of rac)3-Substituted 4-Methoxycarbonyl-1,3-thiazolidine-2-thiones via Rearrangement of a Substituted Group from exo-S to N in (rac)2-Substituted Thio-4-methoxycarbonyl-$\Delta^2$-1,3-thiazolines[1,2]", 1988; pp. 495-508, Chem.Pharm.Bull.36(2).
Regina Zibuck et al, "Total Synthesis of (+)-Latrunculin B", 1986, 2451-2453, J. Am.Chem.Soc. 108.

Primary Examiner—Robert Gerstl
Attorney, Agent, or Firm—Frishauf, Holtz, Goodman & Woodward

[57] ABSTRACT

This invention relates to the compounds of the formula [I] and salts thereof, which are useful for treatment of liver disorders,

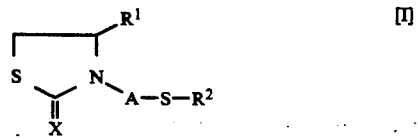

wherein
X is oxygen or sulfur;
R$^1$ is lower alkyl which can be substituted by hydroxy, carboxy or lower alkoxycarbonyl;
R$^2$ is hydrogen, lower alkanoyl, phenyl lower alkanoyl or phenyl lower alkyl, and said phenyl ring of phenyl lower alkanoyl or phenyl lower alkyl can be substituted by lower alkyl or lower alkoxy; and
A is straight or branched C$_1$-C$_6$ alkylene.

7 Claims, No Drawings

N-ALKYL THIAZOLIDINE DERIVATIVES

DETAILED DESCRIPTION OF THE INVENTION

This invention relates to the compounds of the formula [I] and salts thereof (hereinafter referred to as the "Compound"), which are useful for treatment of liver disorders,

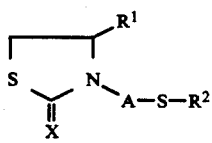

wherein
X is oxygen or sulfur;
$R^1$ is lower alkyl which can be substituted by hydroxy, carboxy or lower alkoxycarbonyl;
$R^2$ is hydrogen, lower alkanoyl, phenyl lower alkanoyl or phenyl lower alkyl, and said phenyl ring of phenyl lower alkanoyl or phenyl lower alkyl can be substituted by lower alkyl or lower alkoxy; and
A is straight or branched $C_1$–$C_6$ alkylene.
The same shall be applied hereinafter.

The terms defined above are explained as follows in more detail. The term "lower alkyl" intends to designates straight or branched $C_1$–$C_6$ alkyl exemplified by methyl, ethyl, propyl, isopropyl and hexyl, "lower alkoxy" intends to designates straight or branched $C_1$–$C_6$ alkoxy exemplified by methoxy, ethoxy, propoxy, isopropoxy or hexyloxy, and "lower alkanoyl" intends to designates straight or branched $C_2$–$C_6$ alkanoyl exemplified by acetyl, propionyl, hexanoyl, isopropionyl and pivaloyl.

The Compound can be converted into pharmaceutically acceptable salts. Examples of the salts are sodium salt, potassium salt, magnesium salt and calcium salt.

There are few studies on N-alkyl-thiazolidine-2-thione derivatives. Only Nagao et al. reported such N-alkyl-thiazolidine derivatives (Chem. Pharm. Bull., 36(2), 495 (1988)). They studied the rearrangement reaction from 2-alkylthiothiazolidine derivatives, which was synthesized by the reaction of thiazolidine-2-thione derivatives with alkyl halide, to N-alkyl-thiazolidine-2-thione.

There are also few studies on N-alkyl-thiazolidine-2-one derivatives. Only N-p-methoxybenzyl derivative was known as a synthetic intermediate of (+)-latrunclin B which is a natural toxin (J. Am. Chem. Soc., 108, 2451 (1986)).

As mentioned above, there are few studies on N-alkyl derivatives of thiazolidine 2-thione (or 2-one), especially compounds having N-alkyl group substituted by a sulfur atom have not been known.

Thereupon, we studied synthetic methods of N-alkyl-thiazolidine-2-thione (or 2-one) derivatives wherein N-alkyl group contains a sulfur atom and have succeeded in obtaining various novel compounds. Furthermore, we studied applications of the Compound to drugs and found that the Compound would be useful for treatment of liver disorders.

The Compound can be prepared by such methods as the follows.

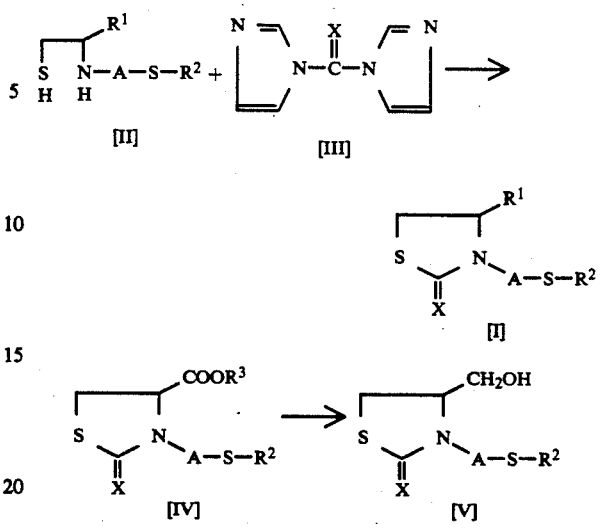

In the formula, $R^3$ is hydrogen or lower alkyl.

The Compound can be prepared by a reaction of the compound of the formula [II] with the compound of the formula [III].

When $R^1$ is carboxy or lower alkoxycarbonyl in the formula [I], if necessary, the compound can be reduced and convert into the compound of the formula [V], which is included in this invention, with reducing reagent such as lithium aluminium hydride.

When $R^2$ in the formula [I] or [V] is lower alkanoyl, phenyl lower alkanoyl or phenyl lower alkyl and intended to use as a protective group, the protective group can be removed by a known method to give thiol compound.

The Compound has stereoisomers because of the existence of one or more asymmetric carbon atom, and these isomers are included in this invention.

The Compound is useful as a medical substance, especially for treatment of liver disorders such as acute hepatic failure, acute hepatitis, chronic hepatitis and liver cirrhosis.

The acute hepatic failure model reported by Feruluga J. et al., (Agent and Actions, 9, 566 (1979)) is known as an animal model to examine effects of a drug on liver disorders. We examined effects of the Compound on liver disorders using this model. As the result of our experiment, we found that the mortality of the animal group treated with the Compound was lower than that of the control group. The result proves that the Compound is useful for treatment of liver disorders.

The Compound can be administered either orally or parenterally. Examples of dosage forms are tablet, capsule, powders, granules, injection and the percutaneous. The dosage is adjusted depending on symptom, dosage form, etc., but usual daily dosage is 1 to 5000 mg in one or a few divided doses.

Examples of formulations are shown below.

1) Tablet

The following tablet can be prepared by a usual method.

| Compound | 100 mg |
|---|---|
| crystalline cellulose | 20 mg |
| lactose | 40 mg |
| hydroxypropylcellulose | 5 mg |

| | |
|---|---|
| magnesium stearate | 5 mg |
| total | 170 mg |

2) Capsule

The following capsule can be prepared by a usual method.

| | |
|---|---|
| Compound | 5 mg |
| lactose | 142 mg |
| magnesium stearate | 3 mg |
| total | 150 mg |

By changing the ratio of the Compound and lactose, capsules which contains 10 mg, 30 mg, 50 mg or 100 mg of the Compound, can be prepared.

3) Granules

The following granules can be prepared by a usual method.

| | |
|---|---|
| Compound | 50 mg |
| lactose | 55 mg |
| starch | 20 mg |
| hydroxypropylcellulose | 4 mg |
| talc | 1 mg |
| total | 130 mg |

Examples of preparations of the Compound are shown below.

EXAMPLE

Example 1

(4R)-3-[2-(4-methoxybenzylthio)-2-methylpropyl]-4-methoxycarbonylthiazolidine-2-thione (compound No. 1)

To a solution of N-[2-(4-methoxybenzylthio)-2-methylpropyl]-L-cysteine methyl ester (5.0 g) in chloroform (90 ml), thiocarbonyldiimidazole (3.0 g) was added and the mixture was stirred for 1 hr at room temperature. The reaction mixture was washed with 3N hydrochloric acid, water and then saturated sodium chloride solution, dried over anhydrous magnesium sulfate, and concentrated in vacuo. The crude product was recrystallized from ethyl acetate to give 5.1 g (91%) of the titled compound.

m.p. 125°–127° C. ( ethyl acetate )
$[\alpha]_D^{25}$ −63.7°( c=1.0, chloroform )
IR (KBr, cm$^{-1}$) 2964, 1743, 1609, 1514, 1443, 1408, 1303, 1242, 1217, 1177, 1130, 1032, 990, 838.

By the similar method as Example 1, following compounds were obtained.

(4R)-3-[2,2-dimethyl-3-(4-methoxybenzylthio)propyl]-4-methoxycarbonylthiazolidine-2-thione (compound No.2)

$[\alpha]_D^{25}$ −13.7°( c=1.0, chloroform )
IR (Film, cm$^{-1}$) 2952, 1743, 1608, 1510, 1444, 1401, 1300, 1201, 1029, 986, 832.

(4R)-3-[3-(4-methoxybenzylthio)propyl]-4-methoxycarbonylthiazolidine-2-thione (compound No.3)

m.p. 57°–59° C. ( n-hexane - ethyl acetate )
$[\alpha]_D^{25}$ −41.2°( c=1.0, chloroform )
IR (KBr, cm$^{-1}$) 2952, 2908, 1735, 1609, 1514, 1467, 1424, 1350, 1298, 1207, 1147, 1065, 993.

(4R)-3-[2-(4-methoxybenzylthio)propyl]-4-methoxycarbonylthiazolidine-2-thione diastereomer-A (compound No.4)

m.p. 60°–62° C. ( n-hexane - ethyl acetate )
$[\alpha]_D^{25}$ −76.9°( c=1.0, chloroform )
IR (KBr, cm$^{-1}$) 2972, 1731, 1610, 1514, 1406, 1287, 1253, 1210, 1173, 1115, 1032, 844.

diastereomer-B (compound No.5)

$[\alpha]_D^{25}$ −94.4°( c=1.0, chloroform )
IR (Film, cm$^{-1}$) 2952, 1746, 1610, 1513, 1452, 1246, 1205, 1177, 1107, 1030, 986, 835.

(4R)-3-[3-(4-methoxybenzylthio)-3-methylbutyl]-4-methoxycarbonylthiazolidine-2-thione (compound No.6)

m.p. 81°–83° C. ( n-hexane - ethyl acetate )
$[\alpha]_D^{25}$ −36.8°( c=1.0, chloroform )
IR (KBr, cm$^{-1}$) 2956, 1752, 1611, 1514, 1465, 1417, 1366, 1225, 1172, 1035, 973, 917, 838, 744.

(4R)-3-(2-acetylthio-2-methylpropyl)-4-methoxycarbonylthiazolidine-2-thione (compound No.7)

m.p. 63°–64° C. ( n-hexane - isopropylether )
$[\alpha]_D^{25}$ −49.0°( c=0.5, chloroform )
IR (KBr, cm$^{-1}$) 2966, 1737, 1685, 1444, 1407, 1350, 1304, 1224, 1110, 1060, 993, 942, 877, 688, 631.

(4R)-3-[3-(4-methoxybenzylthio)-2-methylpropyl]-4-methoxycarbonylthiazolidine-2-thione diastereomer-A (compound No.8)

$[\alpha]_D^{25}$ −24.0°( c=1.1, chloroform )
IR (Film, cm$^{-1}$) 2955, 2835, 1746, 1609, 1511, 1462, 1300, 1245, 1175, 1033, 987, 834.

diastereomer-B (compound No.9)

$[\alpha]_D^{25}$ −84.8°( c=1.0, chloroform )
IR (Film, cm$^{-1}$) 2955, 2835, 1746, 1609, 1511, 1462, 1416, 1300, 1247, 1176, 1033, 987, 834.

(4R)-3-[2-(4-methoxybenzylthio)ethyl]-4-methoxycarbonylthiazolidine-2-thione (compound No.10)

$[\alpha]_D^{25}$ −65.9°( c=1.0, chloroform )
IR (Film, cm$^{-1}$) 2952, 2834, 1747, 1609, 1511, 1462, 1247, 1175, 1032, 834.

(4R)-3-[2-ethyl-2-(4-methoxybenzylthio)butyl]-4-methoxycarbonylthiazolidine-2-thione (compound No.11)

$[\alpha]_D^{25}$ −36.7°( c=1.0, chloroform )
IR (CHCl$_3$, cm$^{-1}$) 2972, 1745, 1610, 1512, 1442, 1410, 1238, 1176, 1059, 1034, 990, 900.

Example 2

(4R)-3-(2-mercapto-2-methylpropyl)-4-methoxycarbonylthiazolidine-2-thione (compound No.12)

To a solution of compound No.1 (1.0 g) in trifluoroacetic acid (4 ml), thioanisole (0.61 ml) and trifluoromethanesulfonic acid (0.46 ml) were added and the mixture was stirred for 15 minutes under ice-cooling. Ice and saturated sodium bicarbonate solution were added into the reaction mixture and the mixture was extracted with ethyl acetate. The organic layer was washed with saturated sodium bicarbonate solution, water and then saturated sodium chloride solution, dried over anhydrous magnesium sulfate, and concentrated in vacuo. The oily residue was purified by a silica gel column chromatography and recrystallized from n-hexane ethyl acetate to give 0.26 g (38%) of the titled compound.

m.p. 126°-127° C. ( n-hexane - ethyl acetate )
$[\alpha]_D^{25}$ −100.2°( c=1.0, chloroform )
IR (KBr, cm$^{-1}$) 2964, 2920, 1736, 1449, 1412, 1326, 1233, 1129, 987, 880, 801.

By the similar method as Example 2, following compounds were prepared using compound No. 2-10.

(4R)-3-(2,2-dimethyl-3-mercaptopropyl)-4-methoxycarbonylthiazolidine-2-thione (compound No.13)

$[\alpha]_D^{25}$ −111.1°( c=1.0, chloroform )
IR (Film, cm$^{-1}$) 2952, 1739, 1445, 1401, 1058, 983, 876.

(4R)-3-(3-mercaptopropyl)-4-methoxycarbonylthiazolidine-2-thione (compound No.14)

$[\alpha]_D^{25}$ −94.4°( c=1.0, chloroform )
IR (Film, cm$^{-1}$) 2948, 1745, 1466, 1416, 1291, 1260, 1225, 1207.

(4R)-3-(2-mercaptopropyl)-4-methoxycarbonylthiazolidine-2-thione diastereomer-A (compound No.15)

$[\alpha]_D^{25}$ −144.6°( c=1.0, chloroform )
IR (Film, cm$^{-1}$) 2952, 1744, 1456, 1404, 1206, 1179, 1150, 1062, 986.

diastereomer-B (compound No.16)

$[\alpha]_D^{25}$ −149.3°( c=1.0, chloroform )
IR (Film, cm$^{-1}$) 2956, 1745, 1456, 1405, 1291, 1209, 1150, 1109, 986.

(4R)-3-(3-mercapto-3-methylbutyl)-4-methoxycarbonylthiazolidine-2-thione (compound No.17)

$[\alpha]_D^{25}$ −84.9°( c=1.0, chloroform )
IR (Film, cm$^{-1}$) 2956, 2924, 1745, 1466, 1415, 1368, 1284, 1209, 1152, 1064, 985.

(4R)-3-(3-mercapto-2-methylpropyl)-4-methoxycarbonylthiazolidine-2-thione diastereomer-A (compound No.18)

$[\alpha]_D^{25}$ −104.3°( c=1.0, chloroform )
IR (Film, cm$^{-1}$) 2956, 2524, 2360, 1746, 1461, 1419, 1293, 1222, 1101, 1060, 1015, 987.

diastereomer-B (compound No.19)

m.p. 71°-72° C. ( n-hexane - ethyl acetate )
$[\alpha]_D^{25}$ −125.5°( c=0.5, chloroform )
IR (Film, cm$^{-1}$) 2956, 2509, 1759, 1458, 1422, 1303, 1272, 1202, 1139, 1062, 988, 883, 670.

(4R)-3-(2-mercaptoethyl)-4-methoxycarbonylthiazolidine-2-thione (compound No.20)

$[\alpha]_D^{25}$ −112.4°( c=1.0, chloroform )
IR (Film, cm$^{-1}$) 2950, 2530, 1747, 1611, 1462, 1350, 1304, 1226, 1071, 988, 918, 846.

Example 3

(4R)-4-hydroxymethyl-3-[2-(4-methoxybenzylthio)-2-methylpropyl]thiazolidine-2-thione (compound No.21)

To a solution of compound No. 1 (2.0 g) in diethylether(10 ml) and tetrahydrofuran (10 ml), lithium aluminum hydrides (0.145 g) was added and the mixture was stirred for 5 hours at room temperature. 1N hydrochloric acid was added into the reaction mixture and the mixture was extracted with ethyl acetate. The organic layer was washed with 1N hydrochloric acid, water and then saturated sodium chloride solution, dried over sodium sulfate, and concentrated in vacuo. The oily residual was purified by a silica gel column chromatography to give 1.9 g (quantitative yield) of the titled compound.

$[\alpha]_D^{25}$ −31.5°( c=1.0, chloroform )
IR (Film, cm$^{-1}$) 3396, 2960, 1610, 1512, 1456, 1247, 1177, 1129, 1032, 834.

Example 4

(4R)-4-hydroxymethyl-3-(2-mercapto-2-methylpropyl)-thiazolidine-2-thione (compound No. 22)

To a solution of compound No.21 (1.5 g) in trifluoroacetic acid (6 ml), thioanisole (0.74 ml) and trifluoromethanesulfonic acid (0.56 ml) were added and the mixture was stirred for 30 minutes. Ice and sodium bicarbonate solution were added into the reaction mixture and the mixture was extracted with ethyl acetate. The organic layer was washed with saturated sodium bicarbonate solution, water and then saturated sodium chloride solution, dried over magnesium sulfate, and concentrated in vacuo. The oily residue was purified by a silica gel column chromatography to give 0.47 g (47%) of the titled compound.

$[\alpha]_D^{25}$ −73.3°( c=1.0, chloroform )
IR (Film, cm$^{-1}$) 3384, 2964, 2924, 1449, 1409, 1388, 1249, 1194, 1131, 1036.

Example 5

(4R)-3-[2-(4-methoxybenzylthio)-2-methylpropyl]-4-methoxycarbonylthiazolidine-2-one (compound No.23)

To a solution of N-[2-(4-methoxybenzylthio)-2-methylpropyl]-L-cysteine methyl ester (0.5 g) in dimethylformamide (10 ml), carbonyldiimidazole (0.28 g) was added and the mixture was stirred for 2.5 hours at 100°-110° C. 1N hydrochloric acid was added into the reaction mixture and the mixture was extracted with ethyl acetate. The organic layer was washed with 1N hydrochloric acid, water and then saturated sodium chloride solution, dried over magnesium sulfate, and concentrated in vacuo. The oily residue was purified by a silica gel column chromatography and recrystallized from n-hexane—isopropanol to give 0.22 g (40%) of the titled compound.

m.p. 51°-54° C. ( n-hexane - isopropanol )
$[\alpha]_D^{25}$ −49.9°( c=0.25, chloroform )
IR (KBr, cm$^{-1}$) 2964, 1738, 1685, 1510, 1448, 1383, 1333, 1231, 1189, 1120, 1034, 833.

Pharmacological Test

The acute hepatic failure model reported by Feruluga J. et al., (Agent and Actions, 9, 566 (1979)) is known as an animal model to examine effects of a drug on liver disorders. We examined effects of the Compound on liver disorders using this model.

Experimental Method

According to the method described in the literature, 0.7 mg/mouse of Propionibacterium acnes was injected intravenously into male BALB/c strain mice ( 8 weeks old ). Seven days later, the Compound suspended in 1% methylcellulose solution was administered orally at a dose of 100 mg/kg. To a control group, 1% methylcellulose solution alone was administered. One hour later, 25 μg of lipopolysaccharide was injected intravenously, and then the mortality was recorded during 48 hours.

Result

The mortality of the group treated with the Compound was lower than that of the control group.

What we claim is:

1. A compound of the formula [I] and or pharmaceutically acceptable salts thereof,

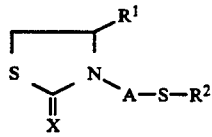

wherein

X is oxygen or sulfur;

$R^1$ is lower alkyl which can be substituted by hydroxy, carboxy or lower alkoxycarbonyl;

$R^2$ is hydrogen, lower alkanoyl, phenyl lower alkanoyl or phenyl lower alkyl, and said phenyl ring of phenyl lower alkanoyl or phenyl lower alkyl can be substituted by lower alkyl or lower alkoxy; and A is straight or branched $C_1$–$C_6$ alkylene.

2. The compound as claimed in claim 1 wherein X is oxygen; $R^1$ is methoxycarbonyl; $R^2$ is 4-methoxybenzyl; and A is straight or branched $C_4$ alkylene.

3. The compound as claimed in claim 1 wherein X is sulfur; $R^1$ is methoxycarbonyl or hydroxymethyl; $R^2$ is hydrogen, 4-methoxybenzyl or acetyl; and A is straight or branched $C_2$–$C_6$ alkylene.

4. The compound as claimed in claim 1 in the form of a sodium salt, potassium salt, magnesium salt or calcium salt.

5. The compound as claimed in claim 1, designated (4R)-3-(2-mercapto-2-methylpropyl) -4-methoxycarbonylthiazolidine-2-thione.

6. The compound as claimed in claim 1, designated (4R)-3-(3-mercaptopropyl)-4-methoxycarbonylthiazolidine-2-thione.

7. A pharmaceutical composition comprising a compound of the formula defined below or pharmaceutically acceptable salts thereof and a pharmaceutically acceptable carrier;

compound of formula I:

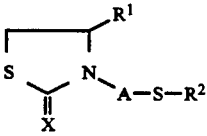

wherein

X is oxygen or sulfur;

$R^1$ is lower alkyl which can be substituted by hydroxy, carboxy or lower alkoxycarbonyl;

$R^2$ is hydrogen, lower alkanoyl, phenyl lower alkanoyl or phenyl lower alkyl, and said phenyl ring of phenyl lower alkanoyl or phenyl lower alkyl can be substituted by lower alkyl or lower alkoxy; and A is straight or branched $C_1$–$C_6$ alkylene.

* * * * *